United States Patent
Kaneko et al.

(10) Patent No.: US 11,543,139 B2
(45) Date of Patent: Jan. 3, 2023

(54) SAFETY CABINET

(71) Applicant: Hitachi Industrial Equipment Systems Co., Ltd., Tokyo (JP)

(72) Inventors: Takeshi Kaneko, Tainai (JP); Hirotoshi Sato, Tokyo (JP); Masashi Takasawa, Tokyo (JP)

(73) Assignee: Hitachi Industrial Equipment Systems Co., Ltd., Tokyo (JP)

( * ) Notice: Subject to any disclaimer, the term of this patent is extended or adjusted under 35 U.S.C. 154(b) by 380 days.

(21) Appl. No.: 16/955,281

(22) PCT Filed: Feb. 4, 2019

(86) PCT No.: PCT/JP2019/003910
§ 371 (c)(1),
(2) Date: Jun. 18, 2020

(87) PCT Pub. No.: WO2019/207895
PCT Pub. Date: Oct. 31, 2019

(65) Prior Publication Data
US 2020/0393147 A1 Dec. 17, 2020

(30) Foreign Application Priority Data

Apr. 24, 2018 (JP) .............................. JP2018-083425

(51) Int. Cl.
*F24F 3/163* (2021.01)
*F24F 11/32* (2018.01)
(Continued)

(52) U.S. Cl.
CPC ................ *F24F 3/163* (2021.01); *B01L 1/00* (2013.01); *C12M 25/16* (2013.01); *C12M 33/04* (2013.01);
(Continued)

(58) Field of Classification Search
None
See application file for complete search history.

(56) References Cited

U.S. PATENT DOCUMENTS 6,615,679 B1 * 9/2003 Knollenberg ........ G01N 1/2247
73/28.01
2005/0048899 A1 3/2005 Anezaki et al.
(Continued)

FOREIGN PATENT DOCUMENTS

| CN | 1576738 A | 2/2005 |
| CN | 101224437 A | 7/2008 |

(Continued)

OTHER PUBLICATIONS

International Search Report (PCT/ISA/210) issued in PCT Application No. PCT/JP2019/003910 dated Apr. 9, 2019 with English translation (four (4) pages).
(Continued)

*Primary Examiner* — Nathan L Laughlin
(74) *Attorney, Agent, or Firm* — Crowell & Moring LLP (57) ABSTRACT

An object of the present invention is to provide a safety cabinet capable of controlling the purity during usage. In order to realize the object, the safety cabinet is configured to include an operation space including an operation stage; a front panel formed in a front surface of the operation space; an operation opening provided in a lower portion of the front panel; a suction port that is provided in the vicinity of the operation opening on a front side of the operation stage to lead downward; an air circulation path through which air suctioned from the suction port flows along a lower portion, a back surface, and an upper portion of the operation space; a particle counter; an operation space-air intake port provided in the operation space to take air into the particle
(Continued)

counter; and an introduction pipe that introduces the air into the particle counter from the operation space-air intake port.

8 Claims, 5 Drawing Sheets

(51) Int. Cl.
*F24F 11/52* (2018.01)
*B01L 1/00* (2006.01)
*C12M 1/12* (2006.01)
*C12M 1/26* (2006.01)
*F24F 110/64* (2018.01)

(52) U.S. Cl.
CPC ............. *C12M 37/00* (2013.01); *F24F 11/32* (2018.01); *F24F 11/52* (2018.01); *F24F 2110/64* (2018.01)

(56) References Cited

U.S. PATENT DOCUMENTS

| | | | |
|---|---|---|---|
| 2005/0245188 A1* | 11/2005 | Wu | F24F 3/163 454/49 |
| 2008/0150404 A1 | 6/2008 | Ono | |
| 2015/0056909 A1* | 2/2015 | Chien | F24F 11/30 454/187 |
| 2018/0001315 A1 | 1/2018 | Kaneko et al. | |
| 2018/0214861 A1 | 8/2018 | Ono et al. | |
| 2019/0310177 A1 | 10/2019 | Ono et al. | |

FOREIGN PATENT DOCUMENTS

| | | |
|---|---|---|
| CN | 205199552 U | 5/2016 |
| CN | 205593887 U | 9/2016 |
| CN | 106140330 A | 11/2016 |
| CN | 107073467 A | 8/2017 |
| JP | 2005-48970 A | 2/2005 |
| JP | 2006-43569 A | 2/2006 |
| JP | 2016-165249 A | 9/2016 |
| JP | 2017-78527 A | 4/2017 |
| WO | WO 2016/079777 A1 | 5/2016 |
| WO | WO 2016/143228 A1 | 9/2016 |
| WO | WO 2018/047409 A1 | 3/2018 |

OTHER PUBLICATIONS

Japanese-language Written Opinion (PCT/ISA/237) issued in PCT Application No. PCT/JP2019/003910 dated Apr. 9, 2019 (five (5) pages).

Chinese-language Office Action issued in Chinese Application No. 201980007195.3 dated May 20, 2021 (12 pages).

* cited by examiner

SAFETY CABINET

TECHNICAL FIELD

The present invention relates to a safety cabinet that uses an air barrier to eliminate a contamination risk from outside.

BACKGROUND ART

In the related art, in the fields of industries such as medicine and pharmaceuticals, a safety cabinet is used as a countermeasure against biohazards. In the safety cabinet, an air barrier is provided and an operation is performed in a partitioned space including an opening portion in a part thereof, and thus the safety cabinet has the isolation capability to be able to protect specimen from sundry bacteria from outside.

Patent Document 1 and Patent Document 2 disclose the background art of the technical field. Patent Document 1 discloses a safety cabinet that includes an open duct including a coupling portion connected to an exhaust port of the safety cabinet, an opening portion which is different from the coupling portion and into which air flows, and an exhaust duct. The safety cabinet includes a differential pressure sensor that detects a difference between a pressure in a space where the open duct is disposed and a pressure in the open duct, and detection means for outputting a detection signal when an absolute value of the differential pressure sensor is a predetermined threshold value or less. In addition, Patent Document 2 discloses a technique where see-through windows are provided in a part of a back wall or a side wall of an operation space of the safety cabinet and a part of a main body rear wall or a main body side wall of the safety cabinet which is separated from the back wall or the side wall by a circulation flow path, to allow an operator to see through both walls, a display device is installed in an outside portion of the see-through window, and the operator inserts the arms from a front opening portion of the safety cabinet to perform an operation while seeing the operation space from a front shutter.

CITATION LIST

Patent Document

Patent Document 1: JP 2017-078527 A
Patent Document 2: JP 2016-165249 A

SUMMARY OF THE INVENTION

Problems to be Solved by the Invention

In the safety cabinets disclosed in Patent Document 1 and Patent Document 2 which maintain an internal purity to allow an operation to be safely performed, the purity is controlled only by an operation parameter such as the magnitude of an initial air blow, and the actual control of the purity during usage is not taken into consideration.

The present invention has been in light of the foregoing problem, and an object of the present invention is to provide a safety cabinet capable of controlling the purity during usage.

Solutions to Problems

The present invention has been made in light of the background art and the problem described above, and according to one example of the present invention, there is provided a safety cabinet including: an operation space including an operation stage; a front panel formed in a front surface of the operation space; an operation opening provided in a lower portion of the front panel; a suction port that is provided in the vicinity of the operation opening on a front side of the operation stage to lead downward; an air circulation path through which air suctioned from the suction port flows along a lower portion, a back surface, and an upper portion of the operation space; a particle counter; an operation space-air intake port provided in the operation space to take air into the particle counter; and an introduction pipe that introduces the air into the particle counter from the operation space-air intake port.

Effects of the Invention

According to the present invention, it is possible to provide a safety cabinet capable of controlling the purity during usage.

MODE FOR CARRYING OUT THE INVENTION

Hereinafter, embodiments of the present invention will be described with reference to the drawings.

First Embodiment

First of all, initially, a safety cabinet in the related art which is the premise of the present embodiment will be described.

Figure 1:
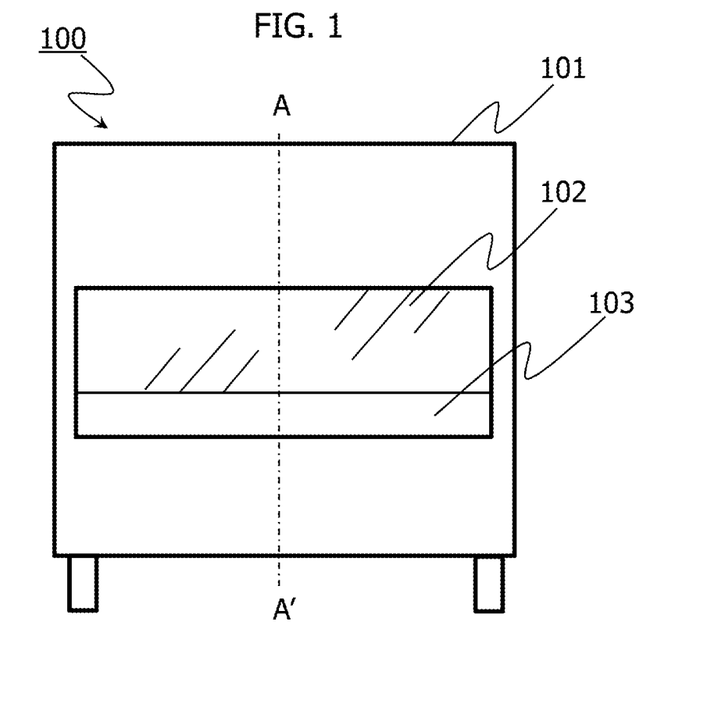
FIG. 1 is a schematic front view of a safety cabinet in the related art.
Figure 2:
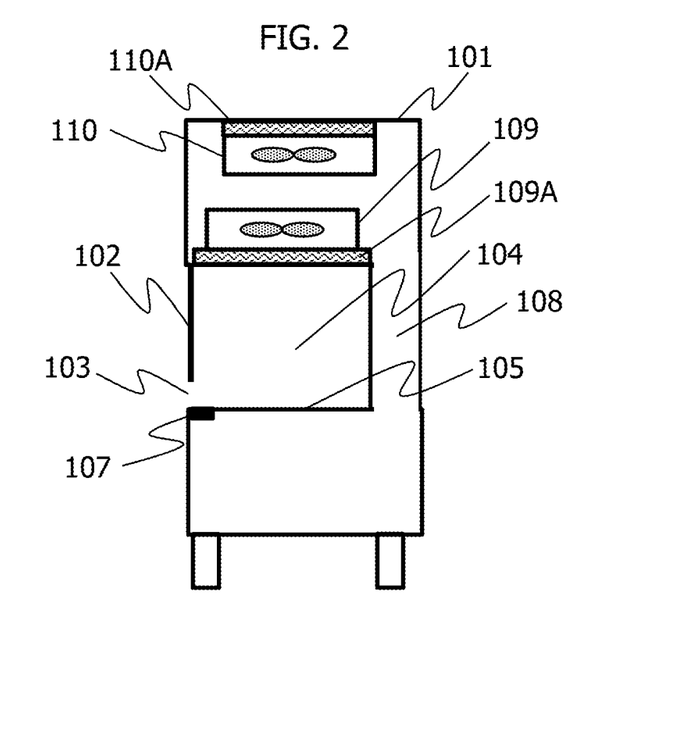
FIG. 2 is a schematic side cross-sectional view of the safety cabinet when a cross section A-A' in FIG. 1 is seen from right.

FIG. 1 illustrates a schematic front view of the safety cabinet. In addition, FIG. 2 illustrates a schematic side cross-sectional view of the safety cabinet when a cross section A-A' in FIG. 1 is seen from right.

An opening is provided in a central region of a housing 101 of a safety cabinet 100, and an operation space 104 is provided therebehind. A front panel 102 is provided on a front surface side of the operation space 104 to block an upper portion of the opening, an operation opening 103 is provided below the front panel 102, and an operator inserts the hands into the operation space 104 from the operation opening 103 to perform an operation. The front panel 102 is made of a transparent material such as a glass, and the operator can see an operation through the front panel.

An operation stage 105 which is substantially flat is provided in a bottom surface of the operation space 104, and the operator performs an operation on the operation stage. A suction port 107 is provided near the operation opening 103 on a front side of the operation stage 105 to lead downward. The suction port 107 is formed as, for example, a slit that extends along the operation opening 103 in a rightward and leftward direction of the housing. A back flow path 108 leading from the suction port 107 to an upper portion of the housing is provided on a back surface side of the operation space 104.

A blowout side fan filter unit (FFU) 109 is provided on an upper side of the operation space 104. The blowout side FFU 109 includes a fan that is rotated by a motor and a filter that removes microparticles, for example, a HEPA filter 109A, and blows out purified air, from which the microparticles have been removed, into the operation space 104. An exhaust side fan filter unit (FFU) 110 is provided in the upper portion of the housing 101, and removes microparticles from a part of air with a filter, for example, a HEPA filter 110A to exhaust the part of air outside the device.

Figure 3:
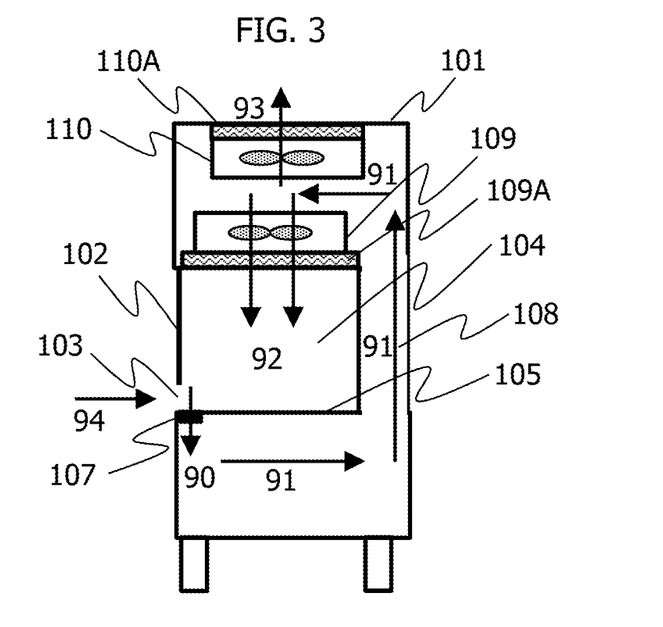
FIG. 3 is a view illustrating an air flow during operation of the safety cabinet in FIG. 2.

In FIG. 3, an air flow during operation of the safety cabinet is indicated by arrows. An air flow 90 which is suctioned from the suction port 107 on a front surface side of the operation stage 105 is blown, as denoted by reference sign 91, into the operation space 104 from the blowout side FFU 109 through a lower portion of the housing, the back flow path 108, and the upper portion of the housing. Since purified air from which the microparticles have been removed by the HEPA filter 109A of the blowout side FFU 109 is blown into the operation space 104, the operation space 104 is maintained in a purified state. In this case, when only an air flow denoted by reference sign 92 flows into the operation space 104, air in the operation space may leak outside, which is a concern. For this reason, the exhaust side FFU 110 is provided to discharge a part of air outside through the HEPA filter 110A. Accordingly, the pressure in the operation space decreases, and an air flow 94 which is to be introduced from outside to inside through the operation opening 103 below the front panel 102 is generated. When the air flow 94 flows into the operation space as it is, the purity of the operation space deteriorates. However, the air volume of the air flow 92 which is blown out into the operation space from the blowout side FFU 109 and the air volume of an air flow 93 which is exhausted outside from the exhaust side FFU 110 are properly controlled, so that all of the air flow 94 flowing in from the operation opening 103 and the majority of the air flow 92 blown into the operation space are suctioned from the suction port 107. Therefore, an atmospheric barrier (air barrier) which prevents the air flow 94 from flowing into the operation space 104 from the operation opening 103 is formed by the air flow 92 which is blown out into the operation space 104. Accordingly, it is possible to realize an equilibrium state where the air from outside does not contaminate the operation space 104 and non-purified inside air does not leak outside.

Accordingly, even when the operator inserts the hands into the operation space 104 through the operation opening 103 to perform an operation, it is possible to realize the maintenance of the purity and the prevention of contamination.

Here, the purity is controlled only by an operation parameter such as the magnitude of an initial air blow, and the actual control of the purity during usage is not taken into consideration.

Therefore, in order to solve the problem, the present embodiment employs a configuration where the safety cabinet is provided with a particle monitor that monitors the number of particles such as waste matter, dirt, foreign matter, and dust. Hereinafter, the configuration will be described in detail.

Figure 4:
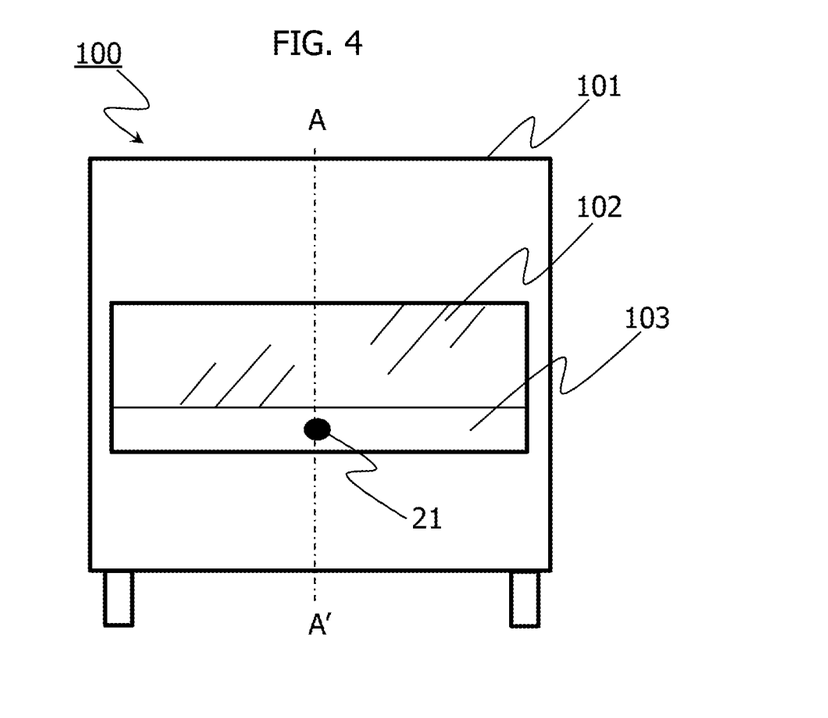
FIG. 4 is a schematic front view of a safety cabinet in a first embodiment.
Figure 5:
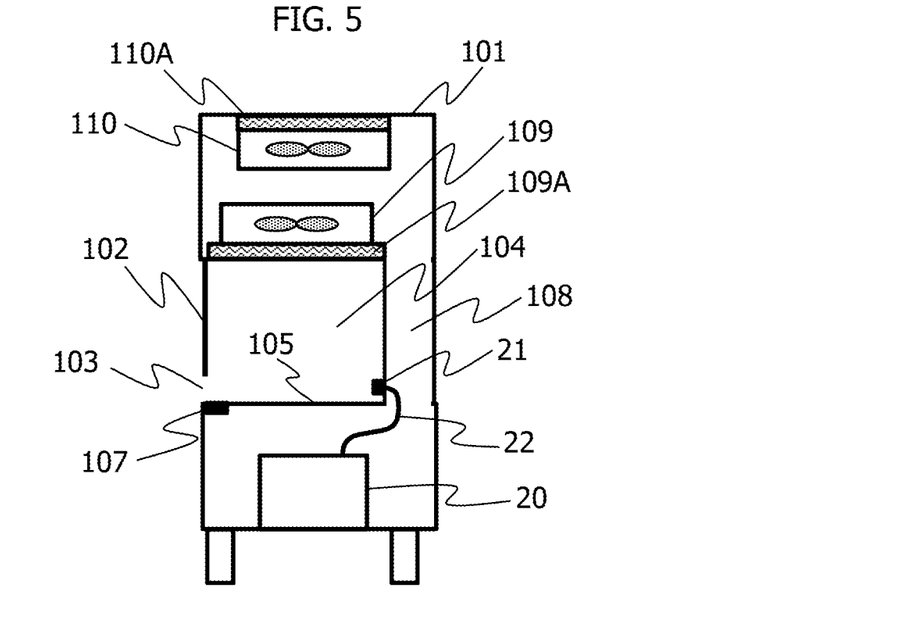
FIG. 5 is a schematic side cross-sectional view of the safety cabinet in the first embodiment.

FIG. 4 is a schematic front view of the safety cabinet in the present embodiment. In addition, FIG. 5 is a schematic side cross-sectional view of the safety cabinet in the present embodiment. In FIGS. 4 and 5, the same reference signs are assigned to components having the same functions as those in FIGS. 1 and 2, and descriptions thereof will be omitted. The point of difference of FIG. 4 from FIG. 1 is that an operation space-air intake port 21 is provided in the operation space 104. In addition, the point of difference of FIG. 5 from FIG. 2 is that a particle counter 20, the operation space-air intake port 21, and an introduction pipe 22 are provided.

In FIGS. 4 and 5, the particle counter 20 is a measuring instrument that counts waste matter, dirt, foreign matter, dust, and the like in the air. The measurement principle thereof is broadly divided into a light scattering method and a light shielding method, and the number of microparticles is measured by capturing an electrical signal proportional to the size of the particle. Air from the operation space-air intake port 21 provided in the operation space 104 is connected via the introduction pipe 22 to the particle counter 20 provided outside the operation space 104. The particle counter suctions air for a certain period of time to measure the number of microparticles in the air.

The number of microparticles measured by the particle counter 20 is compared to a set threshold value by a control device (not illustrated), and when the number of microparticles exceeds the set threshold value, an alarm or a countermeasure is displayed on a display (not illustrated). The set threshold value may be set to the number of microparticles in each purity class that is defined as an air purity class by ISO.

As described above, according to the present embodiment, it is possible to provide the safety cabinet capable of controlling the purity during usage.

Second Embodiment

Figure 6:
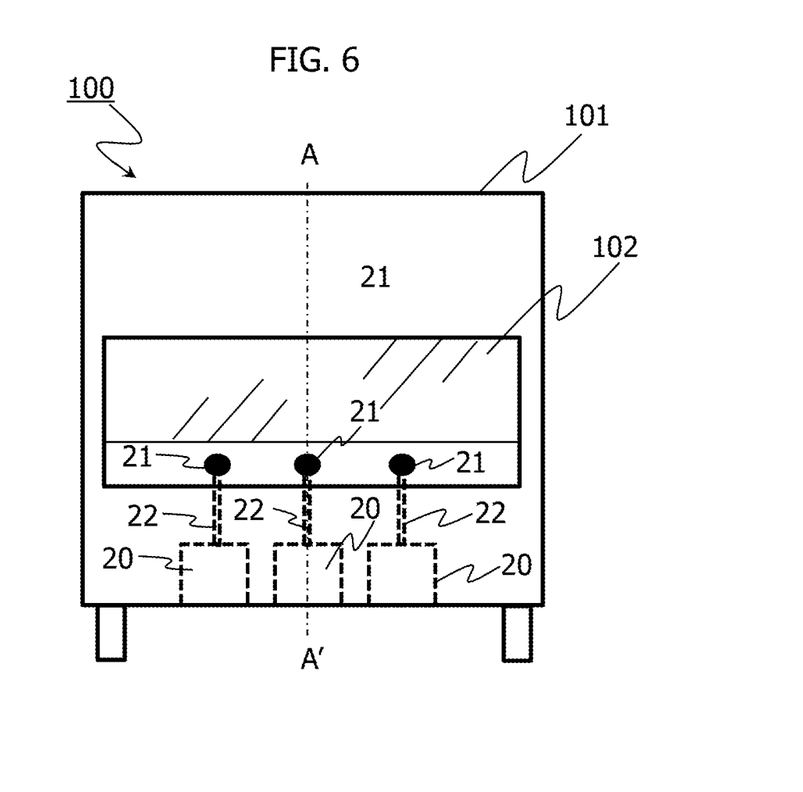
FIG. 6 is a schematic front view of a safety cabinet in a second embodiment.

FIG. 6 is a schematic front view of a safety cabinet in the present embodiment. In FIG. 6, the same reference signs are assigned to components having the same functions as those in FIGS. 4 and 5, and descriptions thereof will be omitted. The point of difference of FIG. 6 from FIGS. 4 and 5 is that a plurality of the operation space-air intake ports 21 are provided and a plurality of the particle counters 20 are provided to correspond to the operation space-air intake ports 21.

Namely, as illustrated in FIG. 6, air from the plurality of operation space-air intake ports 21 is connected via the introduction pipes 22 to the particle counters 20. The particle counters suction air for a certain period of time to measure the number of microparticles in the air from the operation space-air intake ports 21.

According to the present embodiment, it is possible to measure the number of microparticles in the air at a plurality of locations; and thereby, it is possible to provide the safety cabinet capable of more accurately controlling the purity.

Third Embodiment

Figure 7:
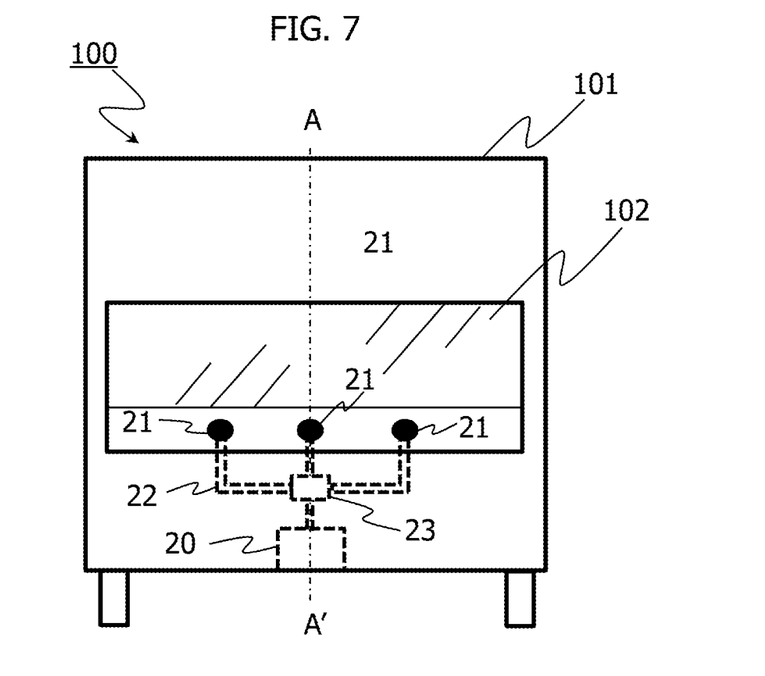
FIG. 7 is a schematic front view of a safety cabinet in a third embodiment.

FIG. 7 is a schematic front view of a safety cabinet in the present embodiment. In FIG. 7, the same reference signs are assigned to components having the same functions as those in FIG. 6, and descriptions thereof will be omitted. The point of difference of FIG. 7 from FIG. 6 is that a branch switching unit 23 is provided to perform switching between air branches from the plurality of introduction pipes 22 connected to the plurality of air intake ports and thus connect an air branch to one particle counter 20.

Namely, the branch switching unit 23 performs switching in a time division manner, so that air at one location can be selectively measured by one particle counter 20.

According to the present embodiment, the number of microparticles in the air at a plurality of locations can be measured by one particle counter; and thereby, it is possible to provide the safety cabinet capable of more accurately controlling the purity with an inexpensive configuration.

Fourth Embodiment

Figure 8:
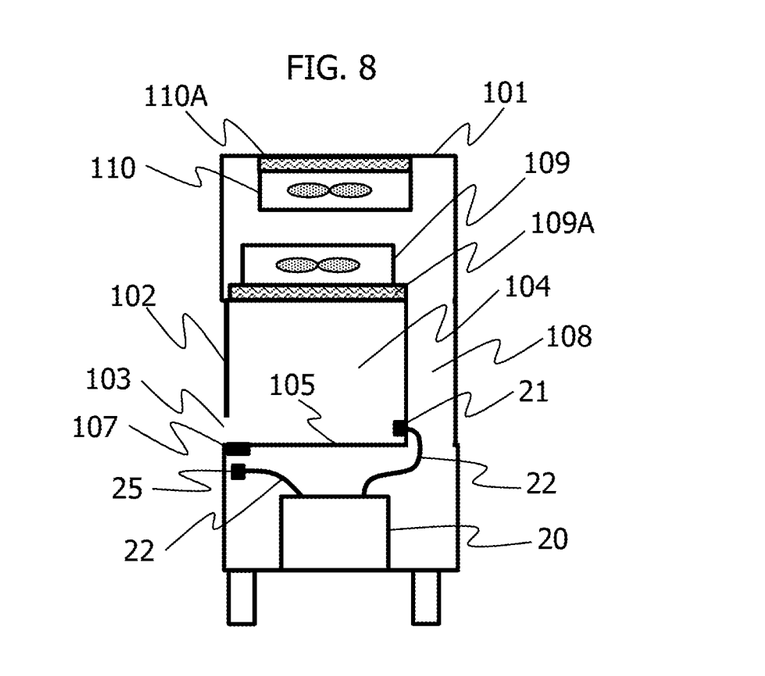
FIG. 8 is a schematic side cross-sectional view of a safety cabinet in a fourth embodiment.

FIG. 8 is a schematic side cross-sectional view of a safety cabinet in the present embodiment. In FIG. 8, the same reference signs are assigned to components having the same functions as those in FIG. 5, and descriptions thereof will be omitted. The point of difference of FIG. 8 from FIG. 5 is that a suction port-air intake port 25 is provided immediately below or on the periphery of the suction port 107 that is provided near the operation opening 103 to lead downward.

Namely, in FIG. 8, the number of microparticles in air from the operation space-air intake port 21 provided in the operation space 104 and in air from the suction port-air intake port 25 provided in the vicinity of the suction port 107 that is provided near the operation opening 103 to lead downward. Here, as with the second and third embodiments, a plurality of the particle counters may be provided to correspond to the air from the operation space-air intake port 21 and the suction port-air intake port 25, or the switching of the branch may be selectively performed in a time division manner and one particle counter may be provided. In FIG. 8, the configuration is not illustrated. As a result, it is possible to monitor the purity in the operation space 104 and of the outside atmosphere, and thus, for example, when the number of microparticles in the air from the suction port-air intake port 25 increases suddenly, it can be found that contamination of the outside becomes severe.

The number of microparticles measured by the particle counter 20 is compared to a set threshold value by the control device (not illustrated). For example, the set threshold value is set to a purity class 5 for the operation space-air intake port 21 side and a purity class 7 for the suction port-air intake port 25 side, and when either purity exceeds the set threshold value, an alarm or a countermeasure is displayed on the display (not illustrated).

For example, even when the purity of the operation space-air intake port 21 side is the purity class 5 or less, in a case where the purity of the suction port-air intake port 25 side is the purity class 7 or higher, it is necessary to secure better purity due to the deterioration of an outside environment. In this case, a purity improvement operation mode is enabled to further prevent air from infiltrating into the operation space 104 from outside.

Figure 9:
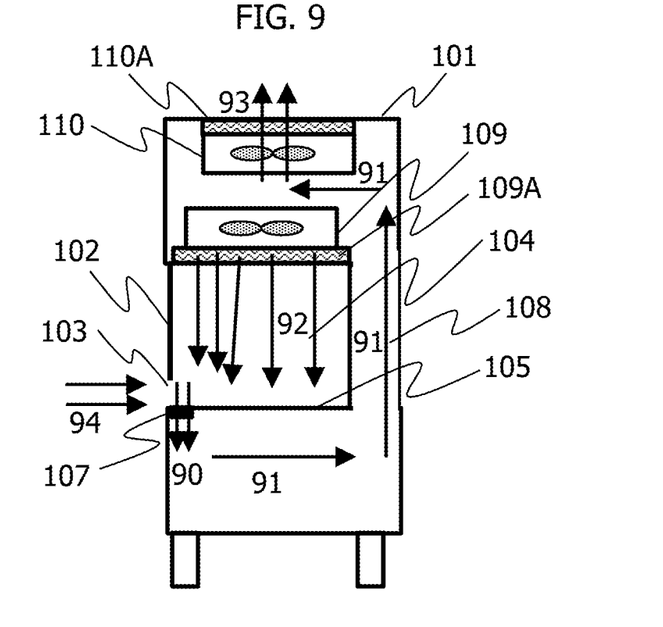
FIG. 9 is a view illustrating an air flow in a purity improvement operation mode of the safety cabinet in the fourth embodiment.

FIG. 9 is a view illustrating an air flow in the purity improvement operation mode of the safety cabinet in the present embodiment. In FIG. 9, the same reference signs are assigned to components having the same functions as those in FIG. 3, and descriptions thereof will be omitted. In FIG. 9, in the purity improvement operation mode, the operation of the exhaust side FFU 110 is enhanced to increase the amount of air to be exhausted outside. Accordingly, the amount of the air flow 90 suctioned from the suction port 107 increases and the air flow 94 flowing in from the operation opening 103 also increases; however, the flow speed of the air flow 92 blown into the operation space increases more greatly in a region near the front panel 102. As a result, the capability of the air barrier is enhanced; and thereby, it is possible to more firmly prevent the outside atmosphere from infiltrating into the operation space 104.

The embodiments have been described above; however, the present invention is not limited to the embodiments and includes various modification examples. For example, the embodiments have been described in detail to facilitate the understanding of the present invention, and the present invention is not necessarily limited to including all of the described configurations. In addition, a part of a configuration of an embodiment can be substituted with a configuration of another embodiment. In addition, a configuration of another embodiment can also be added to a configuration of an embodiment. In addition, another configuration can be added to, deleted from, or substituted with a part of the configuration of each embodiment.

REFERENCE SIGNS LIST

20 Particle counter
21 Operation space-air intake port
22 Introduction pipe
23 Branch switching unit
25 Suction port-air intake port
100 Safety cabinet
101 Housing
102 Front panel
103 Operation opening
104 Operation space
105, 105T Operation stage
107 Suction port
108 Back flow path
109 Blowout side fan filter unit (FFU)
109A Blowout side HEPA filter
110 Exhaust side fan filter unit (FFU)
110A Exhaust side HEPA filter

The invention claimed is:
1. A safety cabinet comprising:
an operation space including an operation stage;
a front panel formed in a front surface of the operation space;
an operation opening provided in a lower portion of the front panel;
a suction port that is provided in the vicinity of the operation opening on a front side of the operation stage to lead downward;
an air circulation path through which air suctioned from the suction port flows along a lower portion, a back surface, and an upper portion of the operation space;
a particle counter;
an operation space-air intake port provided in the operation space to take air into the particle counter;
an introduction pipe that introduces the air into the particle counter from the operation space-air intake port;
a suction port-air intake port provided in the vicinity of the suction port to take air into the particle counter;
a blowout side fan filter unit that is provided on an upper side of the operation space to blow the air out of the air circulation path into the operation space;
an exhaust side fan filter unit that exhausts the air outside from the air circulation path; and a control device,
wherein the control device compares the first number of microparticles in the air from the operation space-air intake port, which is measured by the particle counter, to a first set threshold value and compares the second number of microparticles in the air from the suction port-air intake port, which is measured by the particle counter, to a second set threshold value to enhance an operation of the exhaust side fan filter unit when the first number of microparticles is the first set threshold value or less and the second number of microparticles is the second set threshold value or greater.

2. The safety cabinet according to claim 1, further comprising:
a plurality of the operation space-air intake ports and a plurality of the introduction pipes and the particle counters that correspond to the plurality of operation space-air intake ports.

3. The safety cabinet according to claim 1, further comprising:
a plurality of the operation space-air intake ports;
a plurality of the introduction pipes that correspond to the plurality of operation space-air intake ports; and
a branch switching unit that performs switching between air branches from the plurality of introduction pipes to connect one of the air branches to the particle counter.

4. The safety cabinet according to claim 1, further comprising:
a control device,
wherein the control device compares the number of microparticles, which is measured by the particle counter, to a set threshold value to issue an alarm when the number of microparticles exceeds the set threshold value.

5. The safety cabinet according to claim 1, further comprising:
a control device; and
a display,
wherein the control device compares the number of microparticles, which is measured by the particle counter, to a set threshold value to display a countermeasure on the display when the number of microparticles exceeds the set threshold value.

6. The safety cabinet according to claim 1, further comprising:
an introduction pipe that introduces the air into the particle counter from the suction port-air intake port.

7. The safety cabinet according to claim 6, further comprising:
a second particle counter that takes air from the suction port-air intake port.

8. The safety cabinet according to claim 6, further comprising:
a branch switching unit that performs switching between an air branch from the operation space-air intake port and an air branch from the suction port-air intake port to take one of the air branches into the particle counter.

* * * * *